US00PP11834P2

(12) United States Plant Patent
Williams

(10) Patent No.: US PP11,834 P2
(45) Date of Patent: Apr. 3, 2001

(54) CLIMBING ROSE PLANT NAMED 'SCARLET STAR'

(75) Inventor: J. Benjamin Williams, Silver Spring, MD (US)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/365,182

(22) Filed: Aug. 2, 1999

(51) Int. Cl.[7] ..... A01H 5/00
(52) U.S. Cl. ..... Plt./115
(58) Field of Search ..... Plt./115, 139, 140

*Primary Examiner*—Howard J. Locker
(74) *Attorney, Agent, or Firm*—Burns, Doane, Swecker & Mathis, LLP

(57) ABSTRACT

A new and distinct variety of climbing rose plant is provided which forms in abundance on a substantially continuous basis attractive double blossoms that are bright medium red in coloration. The vegetation is vigorous and the growth habit is upright, bushy, and climbing. Attractive large ornamental foliage that is thick and satiny is formed. Good disease resistance is exhibited. Seed set occurs on a prolific basis. Winter hardiness is very good. Additionally, the new variety is particularly well suited for growing as distinctive ornamentation in the landscape.

2 Drawing Sheets

SUMMARY OF THE INVENTION

The new variety of climbing rose plant of the present invention was created by artificial pollination wherein two parents were crossed which previously had been studied in the hope that they would contribute the desired characteristics. The female parent (i.e., the seed parent) was a seedling of the 'Red Fountain' variety (U.S. Plant Pat. No. 3,615). The male parent (i.e. the pollen parent) of the new variety was the 'Mister Lincoln' variety (U.S. Plant Pat. No. 2,370). The parentage of the new variety can be summarized as follows:

'Red Fountain'×'Mister Lincoln'.

The intent of the breeding program was to create a new rose variety as vigorous as the parent 'Red Fountain' variety with a larger and improved bloom configuration.

The seeds resulting from the above pollination were sown and small plants were obtained which were physically and biologically different from each other. Selective study resulted in the identification of a single plant of the new variety.

It was found that the new variety of climbing rose plant of the present invention possesses the following combination of characteristics:

(a) Abundantly forms attractive medium red double blossoms that are larger and better formed than those of the parent 'Red Fountain' variety, (b) Exhibits an upright climbing growth habit, (c) Forms attractive large ornamental foliage that is thick and satiny, (d) Exhibits a prolific propensity to set seeds, (e) Exhibits good disease resistance,and (f) Is very winter hardy.

The buds of the new variety bear a more traditional configuration and when fully open are less informal than those of the parent 'Red Fountain' variety.

The new variety well meets the needs of the horticultural industry. It can be grown to advantage as attractive ornamentation in parks, gardens, public areas, and residential landscapes. Accordingly, it is particularly well suited for growing as attractive ornamentation in the landscape. The bright medium red blossoms contrast nicely with the glossy green foliage.

The characteristics of the new variety have been found to be homogeneous and are stable and are strictly transmissible by asexual propagation preformed at Wasco, Calif., such as budding, grafting, and cuttage from one generation to another.

The new variety has been named the 'Scarlet Star' variety.

BRIEF DESCRIPTION OF THE PHOTOGRAPHS

The accompanying photographs show, as nearly true as it is reasonably possible to make the same in color illustrations of this character, typical specimens of the plant and plant parts of the new variety. The rose plants of the new variety illustrated in the photographs were three years of age and were grown outdoors during July while gowing on Doctor Huey rootstock at West Grove, Pa.

DETAILED DESCRIPTION

Figure 1:
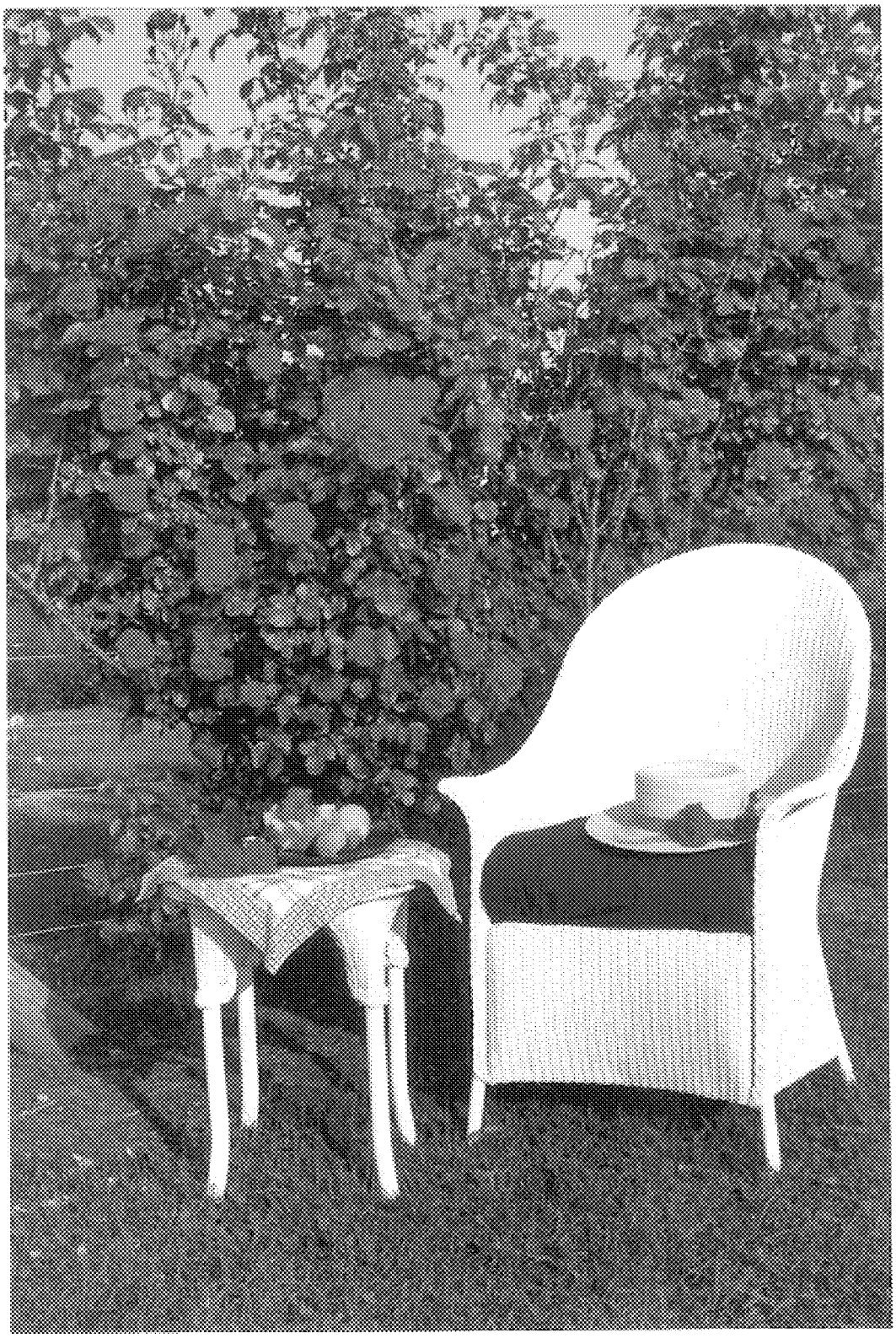
FIG. 1 illustrates the overall plant while being grown on a support in a garden setting.
Figure 2:
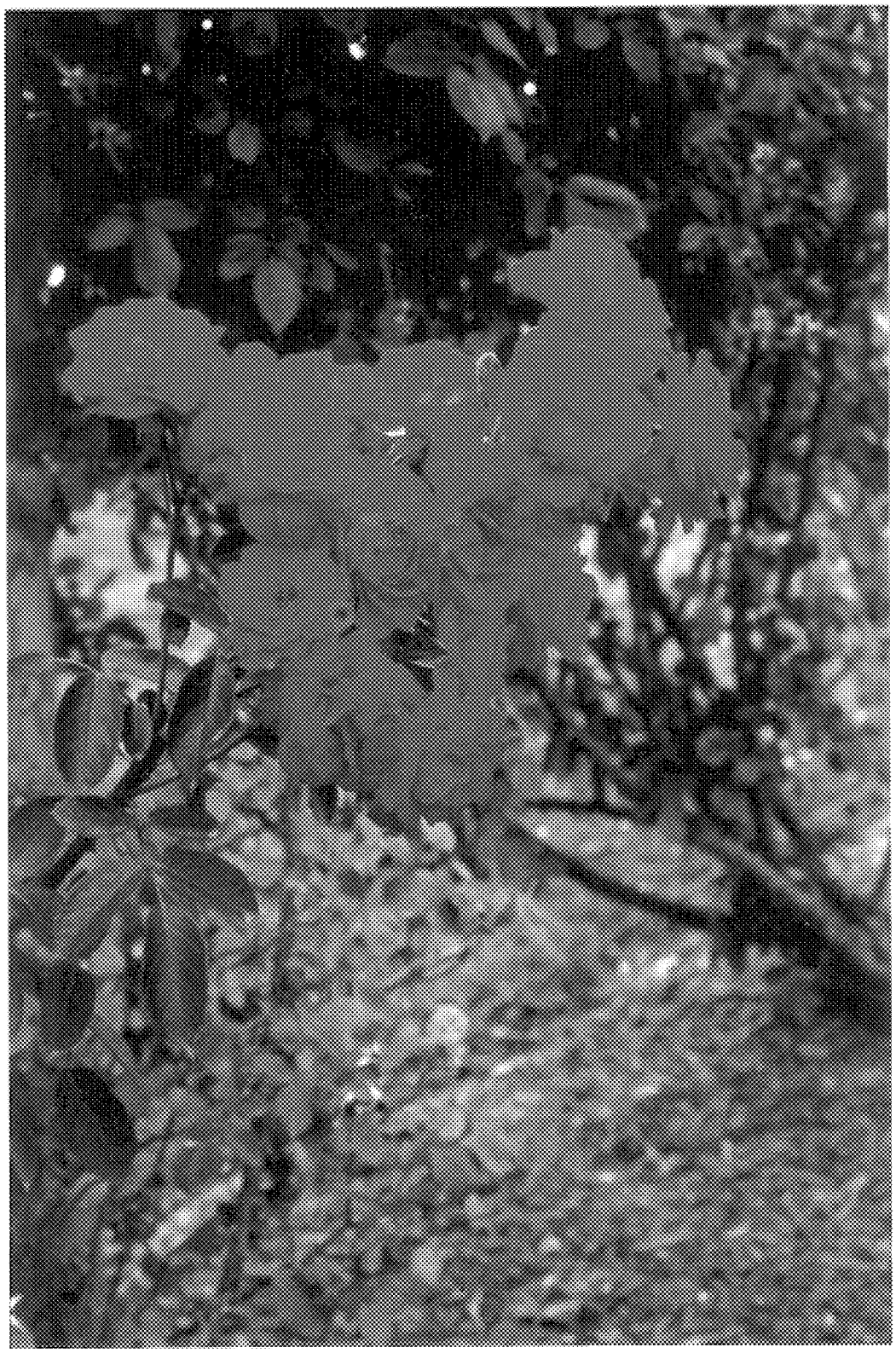
FIG. 2 illustrates a closer view of the attractive medium red blossoms and nicely contrasting foliage.

The chart used in the identification of colors is that of The Royal Horticultural Society (R.H.S. Colour Chart). The description is based on three year-old specimens of the new variety during July while grown outdoors on Doctor Huey rootstock at West Grove, Pa.

Class: Climber.
Plant:

*Height.*—Approximately 12 to 15 feet on average at the end of the growing season.

*Width.*—Approximately 6 to 8 feet on average at the end of the growing season.

*Habit.*—Upright, bushy, climbing.

Branches:

*Color.*—Young stems: Near Yellow-Green Group 144C. Adult wood: Yellow-Green Group 144B.

*Thorns.*—Size: Approximately 1 cm. on average. Configuration: Curved and hooked. Quantity: Approximately 60 true thorns per cutting having a length of 2 feet. Color: Greyed-Yellow Group 162B with tips of Greyed-Orange Group 177A.

Leaves:

*Stipules.*—Middle portion narrows downward and the margin is comb-shaped.

*Petioles.*—Upper surface: Yellow-Green Group 144C with some prickles. Under surface: Yellow-Green Group 144B.

*Leaflets.*—Number: 3 and 5. Shape: Ovate with a serrulate margin, rounded base, and acuminate tip. Serration: Serrulate. Texture: Thick and consistent. Overall appearance: Medium green in coloration, with a satiny finish. Color (young foliage): Upper surface: Yellow-Green Group 146C with margins of Greyed-Purple Group 185C. Under surface: Yellow-Green Group 146D with highlights of Greyed-Purple Group 185C. Color (adult foliage): Upper surface: Green Group 137B. Under surface: Yellow-Green Group 146C.

Inflorescence:

*Number of flowers.*—Commonly approximately 5 blooms on average in a cluster.

*Peduncle.*—Medium, Yellow-Green Group 144C with some prickles, and approximately 4 cm. in length.

*Sepals.*—Upper surface: Yellow-Green Group 145B with pubescence of White Group 155D. Under surface: Yellow-Green Group 144B.

*Buds.*—Shape: Pointed. Length: Approximately 2 cm. on average. Size: Small to medium. Color (when opening): Upper surface: Red Group 45B. Under surface: Commonly between Red Group 53B and Red Group 53C.

*Flower.*—Form: Double and somewhat informal when fully open. Diameter: Approximately 7 cm. on average. Color (when opening begins): Upper surface: Red Group 45B. Under surface: Between Red Group 53B and Red Group 53C. Color (when blooming): Upper surface: Between Red Group 46B and Red Group 46C. Under surface: Red Group 53C with highlights of Red Group 53D. Color (at end of blooming): Upper surface: Between Red Group 53C and Red Group 53D. Under surface: Red Group 53D with highlights of Red Group 54B. Fragrance: Slightly spicy. Lasting quality: Approximately 10 days on the plant and approximately 5–6 days when cut and placed in a vase. Petal form: Wedge-shaped with a curled apex. Petal number: Approximately 20 to 25 on average. Stamen number: Approximately 40 on average. Anthers: Greyed-Yellow Group 165A in coloration. Filaments: Greyed-Orange Group 165C. Pistils: Approximately 30 on average. Stigmas: Greyed-Orange Group 163C in coloration. Styles: Red Group 43D in coloration. Receptacle: Separate and free with achenes on the bottom and wall.

Development:

*Vegetation.*—Vigorous and strong.

*Blossoming.*—Abundant and substantially continuous.

*Resistance to diseases.*—Good, particularly with respect to Powdery Mildew and Blackspot.

*Hardiness.*—Very good, grows well in U.S.D.A. Hardiness Zone Nos. 4 to 9.

I claim:

1. A new and distinct variety of climbing rose plant characterized by the following combination of characteristics:

(a) Abundantly forms attractive medium red double blossoms that are larger and better formed than those of the parent 'Red Fountain' variety, (b) Exhibits an upright climbing growth habit, (c) Forms attractive large ornamental foliage that is thick and satiny, (d) Exhibits a prolific propensity to set seeds, (e) Exhibits good disease resistance, and (f) Is very winter hardy:

substantially as herein shown and described.

* * * * *